United States Patent [19]

Arai

[11] Patent Number: 4,939,085

[45] Date of Patent: Jul. 3, 1990

[54] OXIDIZED COENZYME-CONTAINING DRY ANALYTICAL ELEMENT

[75] Inventor: Fuminori Arai, Asaka, Japan

[73] Assignee: Fuji Photo Film Co., Ltd., Kanagawa, Japan

[21] Appl. No.: 107,673

[22] Filed: Oct. 9, 1987

[30] Foreign Application Priority Data

Oct. 9, 1986 [JP] Japan ................................ 61-240287

[51] Int. Cl.$^5$ .............................................. C12Q 1/32
[52] U.S. Cl. ......................................... 435/26; 422/56; 422/57; 435/11; 435/25; 435/805; 436/71; 436/169; 436/170; 436/904
[58] Field of Search ...................... 422/56, 57; 435/11, 435/25, 26, 805; 436/71, 169, 170, 904

[56] References Cited

U.S. PATENT DOCUMENTS

| | | | |
|---|---|---|---|
| 3,867,258 | 2/1975 | Forgione | 435/26 X |
| 3,956,069 | 5/1976 | Allain et al. | 435/26 X |
| 3,992,158 | 11/1976 | Przybylowicz et al. | 422/57 |
| 4,241,179 | 12/1980 | Madappally et al. | 435/26 X |
| 4,381,921 | 5/1983 | Pierce et al. | 436/535 |
| 4,613,569 | 9/1986 | Geisler et al. | 435/26 |
| 4,629,697 | 12/1986 | Limbach et al. | 422/56 X |

OTHER PUBLICATIONS

"Lactate Dehydrogenase" in *Kodak Rate Methodologies Brochure*, Jul. 1986, MP 2–75.

*Primary Examiner*—Robert J. Warden
*Assistant Examiner*—Carol A. Spiegel
*Attorney, Agent, or Firm*—McAulay Fisher Nissen & Goldberg

[57] ABSTRACT

A dry analytical element having functional layers which contain dehydrogenase, oxidized nicotinamide coenzyme, pyruvate, an electron transport compound and an electron acceptable dye-forming compound is disclosed. The improvement the analytical element resides in that the coenzyme and dye-forming compound are contained in one or two layers which are different from a layer containing pyruvate.

10 Claims, No Drawings

OXIDIZED COENZYME-CONTAINING DRY ANALYTICAL ELEMENT

BACKGROUND OF THE INVENTION

1. Field of the Invention

The present invention relates to a dry multilayer analytical element containing an oxidized coenzyme and a process for the preparation of said element.

2. Description of Prior Art

Reactions in which dehydrogenase and a coenzyme are involved have been widely employed in clinical chemical analyses. For example, various reaction systems in which a dehydrogenase such as glycerol dehydrogenase, cholesterol dehydrogenase, lactate dehydrogenase, alcohol dehydrogenase, glutamate dehydrogenase, aldehyde dehydrogenase, α-glycerophosphate dehydrogenase or glucose-6-phosphate dehydrogenase participates are employed for quantitative determination of substrate such as triglyceride, glycerol, cholesterol, lactic acid, glutamate, glycerol-3-phosphoric acid or glucose-6-phosphoric acid, and an enzyme such as aspartic acid aminotransferase (AST), lactate dehydrogenase (LDH), amylase or creatine kinase (CK). Through the reaction, quantitative analysis can be made by directly measuring increase or decrease of the amount of a reduced coenzyme. However, the conventionally employed NADH (i.e., nicotinamide adenine dinucleotide) or NADPH (i.e., nicotinamide adenine dinucleotide phosphate) has its maximum absorption peak at approx. 340 nm, and therefore the photometric measurement requires an expensive photometer for the measurement of a light in the ultraviolet region. Another drawback resides in that such measurement of a light in the ultraviolet region is easily influenced by a variety of coexisting compounds.

An alternative photometric analytical method using an electron acceptable dye-forming compound and an electron transmitter (i.e., carrier) in combination for forming a dye having an absorption peak in the visible ray region upon contact with the produced NADH was proposed for replacement of the above-described method of directly measuring the produced NADH (or NADPH). This method, however, has a drawback that a positive error is introduced if a liquid sample contains dehydrogenases other than the dehydrogenase to be analyzed. Particularly, in the case of analyzing a human serum, the electron acceptable dye-forming compound sometimes reacts with a reduced nicotinamide coenzyme produced by reaction with lactate dehydrogenase (LDH) and lactic acid, to give a colored product. Japanese Patent Provisional Publication No. 55(1980)-104899 describes that the erroneous coloring of the electron acceptable dye-forming compound is obviated by incorporating pyruvic acid into the reaction system.

SUMMARY OF THE INVENTION

It has been confirmed that the incorporation of pyruvate into a dry analytical element is generally effective to remove the erroneous coloring of the electron acceptable dye-forming compound. However, it has been noted that the addition of pyruvate into a dry analytical element sometimes gives a negative error where a reaction layer of the element is adjusted to give a low pH condition upon receipt of a liquid sample. Further, it has been noted that the analytical element gives low analytical accuracy where a pyruvate, a nicotinamide coenzyme and an electron acceptable dye-forming compound are together incorporated into one layer of the element, due to occurrence of fog in storage of the analytical element.

Accordingly, an object of the present invention is to provide a dry multilayer analytical element containing dehydrogenase, an oxidized nicotinamide coenzyme, an electron transport compound (electron transmitter compound), pyruvate, and an electron acceptable dye-forming compound as reagent components, which shows a satisfactorily high analytical accuracy.

There is provided by the present invention an improvement of a dry multilayer analytical element comprising a light-transmissive, water-impermeable support and reagent layers provided on the support, the reagent layers containing dehydrogenase, pyruvate, oxidized nicotinamide coenzyme, an electron transport compound (electron transmitter) and an electron acceptable dye-forming compound, wherein the coenzyme and dye-forming compound are contained in one or two layers which are different from a layer containing pyruvate.

DETAILED DESCRIPTION OF THE INVENTION

The present invention can be applied to a variety of known dry analytical elements. Particularly, the invention is advantageously applied to an element comprising a liquid-permeable layer through which any of dehydrogenase, a reduced coenzyme-detector composition and a liquid sample are permeable. The analytical element of the invention has at least two reagent layers provided on the support. The analytical element may contain other functional layers such as, a light-reflecting layer, a porous spreading layer, a light-blocking layer, a filtration layer, a registration layer, a water-absorbing layer, and an undercoating layer. The reagent layer and other functional layer can be constituted to form a single layer. For instance, the porous spreading layer can contain a reagent or a reagent composition to form a reagent layer.

Various multilayer analytical elements are described in more detail, for example, in U.S. Pat. Nos. 3,992,158 and 4,042,335.

Preferred embodiments of constitution of the analytical elements are listed below.

(1) an element comprising two or more reagent layers arranged on the support;
(2) an element comprising a spreading layer serving as a reagent layer and another reagent layer arranged on the support;
(3) an element comprising a spreading layer and two or more reagent layers arranged on the support;
(4) an element comprising a spreading layer, two or more reagent layers and a water-absorbing layer arranged in order on the support;
(5) an element comprising a spreading layer, a reflection layer (or filtration layer), and two or more reagent layers arranged in order on the support; and
(6) an element comprising a spreading layer, a filtration layer, two or more reagent layers, and a water-absorbing layer arranged in order on the support.

In the analytical element of the present invention, at least one reagent layer contains an oxidized nicotinamide coenzyme. The oxidized nicotinamide coenzyme means NAD+ (oxidized nicotinamide adenine dinucleotide) or NADP+ (oxidized nicotinamide adenine dinucleotide phosphate). Use of any of NAD+ and NADP+ can be determined according to the kind of an oxidation-reduction enzyme used as an analyte or a reagent participating in the reaction.

The dry analytical element of the invention contains an electron transmitter compound (i.e., electron carrier) in at least one reagent layer.

The electron transmitter compound serves for receiving an electron from a reduced nicotinamide coenzyme (i.e. electron donor) produced by the reaction of the analyte and then reducing an electron acceptable dye-forming compound. Examples of the electron transmitter compounds include N-methylphenazine methsulfates such as 5-methylphenazinium methylsulfate and 1-methoxy-5-methylphenazinium methylsulfate and diaphorase (dihydrolipoamide reductase, EC 1.6.4.3.).

The dry analytical element of the invention further contains an electron acceptable dye-forming compound as one of the reagent components.

The electron acceptable dye-forming compound is reduced by the electron transmitter compound to form a compound (i.e., dye) which is photometrically detectable in the visible ray region. The electron acceptable dye-forming compound preferably employed in the invention is a tetrazolium salt. Examples of the tetrazolium salts include 3,3'-(3,3'-dimethoxy-4,4'-biphenylene)-bis(2-(p-nitrophenyl)-2H-tetrazolium chloride) (=NBT); 3-(p-indophenyl)-2-(p-nitrophenyl)-5-phenyl-2H-tetrazolium chloride (=INT); 3-(4,5-dimethyl-2-thiazolyl)-2H-tetrazolium bromide (=MTT); 3,3'-(4,4'-biphenylene)-bis(2,5-diphenyl-2H-tetrazolium chloride); 3,3'-(3,3'-dimethoxy-4,4'-biphenylene)-bis(2,5-diphenyl-2H-tetrazolium chloride); and 3,3'-(3,3'-bis(2,5-bis(p-nitrophenyl)-2H-tetrazolium chloride).

The reaction system in which the oxidized nicotinamide coenzyme, electron transmitter compound and electron acceptable dye-forming compound are involved is stated in more detail in A. L. Babson, et al., Clinica Chimica Acta, 12 (1965), 210–215; R. J. Gay, et al., Clinical Chemistry, 14, No. 8 (1968), 740–753; and R. D. Gapps II, et al., Clinical Chemistry, 12, No. 7 (1966), 406–413.

As to the pyruvate, there is no specific limitation, so long as a pyruvate can serve to reduce or remove influence or activity of lactate dehydrogenase (LDH). Generally, an alkali metal salt of pyruvic acid is preferably employed. Most preferred is potassium pyruvate. If it is desired that a high pH value condition is produced in the layers of the analytical element upon receipt of a liquid sample, lithium pyruvate is preferred.

In the analytical element of the present invention, the pyruvate is present not in contact with both the oxidized coenzyme and the electron acceptable dye-forming compound. Accordingly, the pyruvate is incorporated into a layer which is different from a layer or layers containing the oxidized coenzyme and electron acceptable dye-forming compound. The oxidized coenzyme and the electron acceptable dye-forming compound may be contained in the same layer or different layers. For instance, the analytical element can be prepared by forming one or more layers containing the oxidized and electron acceptable dye-forming compound dispersed in a hydrophilic polymer and then coating thereon a dispersion or solution of a pyruvate in an organic solvent which does not cause swelling of the hydrophilic polymer. The process of coating the pyruvate solution or dispersion can be performed in any of known coating methods including spraying. The coated solution or dispersion is then dried to form a pyruvate-containing layer.

The pyruvate is generally contained in the layer in an amount of approx. 50–1,000 mg/m$^2$, preferably in an amount of approx. 100–500 mg/m$^2$.

In the analytical element of the present invention, the oxidation-reduction enzyme for the analyte is incorporated into at least one layer, whereby the concentration or content of an analyte (substance to be assayed) in a liquid sample can be determined. The analytical element of the invention can be used for measurement of concentration or content of any analyte, provided that the analyte reacts with the oxidation-reduction enzyme (dehydrogenase) and the oxidized nicotinamide coenzyme can serve as an electron acceptor. For example, glycerol dehydrogenase is incorporated in the case of measuring concentration of glycerol, and lactate dehydrogenase is incorporated in the case of measuring concentration of lactic acid.

The reaction system employed in the dry analytical element of the invention can be also used in the determination of activities of various oxidation-reduction enzymes contained in a liquid sample. In more detail, the dry analytical element of the invention can be used to determine activity of any oxidation-reduction enzyme (dehydrogenase) in the case that the oxidized nicotinamide coenzyme serves as an electron acceptor. When the analytical element of the invention is used for determination of activity of an oxidation-reduction enzyme, the reaction system is further incorporated with a substrate of an oxidation reaction (dehydrogenation reaction) in which the oxidation-reduction enzyme acts as a catalyst. For example, lactic acid is further incorporated into the reaction system as a substrate in the case of using the analytical element of the invention for the determination of the lactate dehydrogenase activity. In the case of determining activity of glucose-6-phosphate dehydrogenase, glucose-6-phosphoric acid is further incorporated into the reaction system as a substrate.

The material of the support of the analytical element of the invention preferably is a light-transmissive, water-impermeable support.

Examples of the water-impermeable, light-transmissive supports include transparent supports in the form of a film or a sheet made of a polymer such as polyethylene terephthalate, polycarbonate of bisphenol A, polystyrene and cellulose esters (e.g., cellulose diacetate, cellulose triacetate, cellulose acetate propionate etc.). The thickness of the support generally ranges from approx. 50 $\mu$m to approx. 1 mm, preferably from approx. 80 $\mu$m to approx. 300 $\mu$m.

A hydrophilic polymer can be used for the formation of a water-absorbing layer, a reagent layer, a filtration layer and a light-reflecting layer in the analytical element of the invention. The hydrophilic polymer is a natural or synthetic polymer having a swelling ratio of generally approx. 1.5 to 20, preferably approx. 2.5 to 15, at 30° C. in the case of water absorption.

Examples of the hydrophilic polymers include gelatin (e.g., alkali-treated gelatin, acid-treated gelatin and deionized gelatin), gelatin derivatives (e.g., phthalated gelatin), agarose, polyacrylamide, polyvinyl alcohol and polyvinyl pyrrolidone. If necessary, a surfactant (cationic, amphoteric or nonionic surfactant) may be further added to the hydrophilic polymer.

The light-blocking layer is a water-permeable layer in which light-blocking (or light-reflecting) fine particles are dispersed in a small amount of a film-forming hydrophilic polymer binder. The light-blocking layer may function as light-reflecting layer or background layer as well as blocker to the color of an aqueous liquid spotted on the spreading layer, such as the red of hemoglobin in a whole blood sample, when a detectable change (color change or color development etc.) in the water-absorbing layer is measured from the side of the transparent support through reflection photometry.

Preferred examples of light-blocking and light-reflecting particles are fine titanium dioxide particles and fine barium sulfate particles. In the invention, the light-blocking particles can be incorporated into the spreading layer, if desired.

There may be provided an adhesive layer on the water-absorbing layer or optionally added other layers (e.g., light-blocking layer, filtration layer and reagent layer) to enhance the adhesion of the spreading layer.

The adhesive layer is preferably constituted of a hydrophilic polymer which can bond the spreading layer to other layer to make all of the layers integrated when the polymer is wetted or swelled with water. Examples of the hydrophilic polymer include the polymers employable in the water-absorbing layer. Most preferred are gelatin, gelatin derivatives and polyacrylamide. The dry thickness of the adhesive layer generally ranges from approx. 0.5 $\mu$m to approx. 20 $\mu$m, preferably from approx. 1 $\mu$m to approx. 10 $\mu$m.

The adhesive layer may be provided onto other layers as well as the water-absorbing layer. The adhesive layer can be prepared in such a manner that a solution of a hydrophilic polymer and optionally added other agent such as a surfactant is coated on the water-absorbing layer or other layer.

The term "spreading layer" used herein means a layer capable of metering a liquid sample. This function can be said in terms of a layer having a function which is capable of spreading an applied liquid in such a manner that the spread area of the liquid is formed approximately in proportion to the amount of the liquid when the liquid is applied thereon.

The spreading layer can be made of filter paper, nonwoven fabric, woven fabric (e.g., plain woven fabrics such as broadcloth and poplin), knitted fabric (e.g., tricot knitted fabric, double tricot knitted fabric and milanese knitted fabric), glass fiber filter, membrane filter or a three-dimensional lattice structure composed of polymer microbeads as a material constituting a matrix. Preferred are woven fabric and knitted fabric from the viewpoint of preservation of reagents.

When woven fabric or knitted fabric is used as a material of the spreading layer of an integral multilayer analytical element, the fabric is preferably processed to become hydrophilic to enhance the adhesion to an underlying layer. Examples of such process to make the fabric hydrophilic include physical activating process (preferably glow discharge process or corona discharge process) disclosed in Japanese Patent Provisional Publication No. 57(1982)-66359 and hydrophilic polymer permeating process disclosed in Japanese Patent Provisional Publications No. 55(1980)-164356 and No. 57(1982)-66359.

The spreading layer constituted of woven fabric or knitted fabric can be laminated on a water-absorbing layer or an adhesive layer according to the process disclosed in Japanese Patent Provisional Publications No. 55(1980)-164356 and No. 57(1982)-66359. The process is that woven fabric or knitted fabric is laminated under the substantially uniform weak pressure on the wet or swelling buffer layer or adhesive layer which has been still under wet condition after coating or has been supplied with water (or water containing a small amount of a surfactant) after drying.

The spreading layer constituted of a brushed polymer or a membrane filter can be provided according to the process disclosed in Japanese Patent Publication No. 53(1978)-21677, the spreading layer having a three-dimensional lattice structure constituted of polymer microbeads can be provided according to the method disclosed in Japanese Patent Provisional Publication No. 55(1980)-90859, and the reagent sheet or the spreading layer constituted of filter paper or nonwoven fabric can be provided according to the process disclosed in Japanese Patent Provisional Publication No. 57(1982)-148250.

The spreading layer of the analytical element can contain a hydrophilic polymer and/or a surfactant for adjusting its metering property.

Examples of the hydrophilic polymers include cellulose derivatives, polyvinylpyrrolidone, polyvinyl alcohol and polyacrylamide.

As an example of the surfactant, there can be mentioned a nonionic surfactant. Examples of the nonionic surfactants include p-octylphenoxy polyethoxyethanol, p-nonylphenoxy polyethoxyethanol, polyoxyethylene oleyl ether, polyoxyethylene sorbitan monolaurate, p-nonylphenoxy polyglycidol and octyl glucoside.

In the case of using an analyte which hardly permeates an uniformly coated layer of the polymer binder (i.e., case of using a hydrophobic analyte or a high-molecular analyte), the porous spreading layer is preferably incorporated with a portion of reagent components, particularly a decomposing enzyme.

The multilayer analytical element of the present invention can be preferably prepared by a process which comprises the steps of:

forming on said support a reagent layer containing at least said oxidized nicotinamide coenzyme and electron acceptable dye-forming compound dispersed in a hydrophilic polymer;

coating a solution or dispersion containing at least said pyruvate in an organic solvent substantially not causing swelling of the hydrophilic polymer in the underlying reagent layer over the underlying reagent layer;

and drying the coated layers.

The solution or dispersion containing at least pyruvate is preferably incorporated into a porous spreading layer which is previously provided on the reagent layer containing the coenzyme and dye-forming compound.

There is no specific limitation on the organic solvent employable in the process, so long as the solvent satisfies the above-mentioned conditions, but preferably used is a polar solvent having a boiling point of not higher than 100° C. Examples of such polar solvents include lower fatty alcohols (e.g., methanol, ethanol, propanol, butanol and isopropyl alcohol), dialkyl ketones (e.g., acetone), dialkylethers (e.g., dimethyl ether), and fatty cyclic ethers (e.g., tetrahydrofuran and dioxane). Preferred is a fatty alcohol. From the viewpoints of working environment, etc., particularly preferred are alcohols having less toxicity to a human body such as ethanol, propanol, butanol and isopropyl alcohol. The concentration of the solution or dispersion is desired to be as high as possible, provided that the solution or dispersion easily contains its contents and homogeneously permeates the porous spreading layer. Although the concentration of the solution or dispersion depends upon the kinds of the pyruvate and other optionally incorporatable components such as a pH buffer agent and a hydrophilic polymer, the concentration thereof is generally in the range of approx. 0.2 to 10%, preferably in the range of approx. 0.3 to 7%. The solution or dispersion can be prepared according to a known method. The organic solvent may contain water, provided that the incorporation of water does not substantially bring about migration of reagent composition of the underlying layer into the upper layer.

If the spreading layer is incorporated with a surfactant, the surfactant may be incorporated into the layer in the form of a mixture solution containing both a pyruvate (and a pH buffer agent and a hydrophilic polymer, if desired) and the surfactant or in the form of a different solution.

Incorporation of the pyruvate and pH buffer agent into the porous spreading layer is preferably done after laminating the spreading layer on the underlying reagent layer. When the spreading layer is composed of a micro filter, a knitted fabric or a woven fabric, the pyruvate and pH buffer agent can be incorporated into the spreading layer before laminating the layer. In this case, however, it is difficult to control the content of the pyruvate and buffer agent in the porous spreading layer. Accordingly, it is advantageous to incorporate the pyruvate and pH buffer agent into the spreading layer after providing the spreading layer on the previously formed reagent layer (directly or indirectly via an adhesive layer), from the viewpoints of analytical accuracy and manufacturing cost. The pyruvate and pH buffer agent can be incorporated into the spreading layer, for example, by uniformly coating or spraying the agent on the surface of the spreading layer according to a known method. The coated or sprayed buffer agent can be dried by air or under reduced pressure.

It is preferred from the viewpoint of manufacture, packaging, transportation, preservation and measuring operation that an integrated multilayer analytical element of the present invention is cut into pieces of about 15 to 30 mm square or a circle of about 15 to 30 mm in diameter and put in a slide frame to provide an analytical slide as disclosed in Japanese Patent Provisional Publication Nos. 57(1982)-63452 and 54(1979)-156079, Japanese Utility Model Provisional Publication Nos. 56(1981-142454 and 58(1983)-32350 and Japanese Patent Provisional Publication No. 58(1983)-501144.

About 5 to about 30 μl, preferably about 8 to about 15 μl of an aqueous liquid sample is deposited (spotted) on the porous spreading layer of the analytical element, and, if necessary, the analytical element is incubated at a substantially constant temperature of about 20° to 45° C. A detectable change such as color change or color formation in the element is measured (from the side of the light-transmissive support) by reflection photometry to thereby analyze the analyte in the liquid sample by colorimetry.

Example of the present invention and comparison examples are given below.

Example 1

On a surface of a colorless transparent polyethylene terephthalate (PET) film (support) of 180 μm thick having been undercoated with gelatin was coated the following aqueous composition, and the coated layer was dried to form a reagent layer of 12 μm thick for detecting color formation in the support.

| Composition of Coating Solution | |
|---|---|
| Alkali-treated gelatin | 10 g(16 g/m$^2$) |
| Nonylphenoxy polyethoxyethanol (average oxyethylene unit content: 15) | 0.05 g(0.08 g/m$^2$) |
| ATP | 0.9 g(1.44 g/m$^2$) |
| Magnesium sulfate | 0.7 g(1.12 g/m$^2$) |
| Sodium citrate | 2.0 g(3.2 g/m$^2$) |
| NAD | 0.5 g(0.8 g/m$^2$) |
| 3,3'-(3,3'-Dimethoxy-4,4'-biphenylene)-bis[2-(p-nitrophenyl)-2H-tetrazolium] dichloride | 0.2 g(0.32 g/m$^2$) |
| Diaphorase (EC 1.6.4.3) | 2,830 U(4,530 U/m$^2$) |
| Glycerol kinase (EC 2.7.1.30) | 880 U(1,410 U/m$^2$) |
| Glycerol-3-phosphate dehydrogenase (EC 1.1.99.5) | 5,410 U(8,660 U/m$^2$) |
| Water | 80 g |

The aqueous composition was coated in such an amount that the alkali-treated gelatin in the composition was present in an amount of 16 g/m$^2$ (per surface area of the support).

On the surface of the obtained reagent layer was coated the following aqueous composition, to form a light-blocking layer of 7 μm thick on the reagent layer.

| Composition of Coating Solution for Light-blocking Layer | |
|---|---|
| Alkali-treated gelatin | 5 g(2.7 g/m$^2$) |
| Rutile type titanium dioxide | 30 g(16.2 g/m$^2$) |
| Nonylphenoxy polyethoxyethanol (average oxyethylene unit content: 15) | 0.2 g(0.108 g/m$^2$) |
| Water | 60 g |

The aqueous composition was coated in such an amount that the alkali-treated gelatin in the composition was present in an amount of 2.7 g/m$^2$ (per surface area of the support).

On the surface of the obtained light-blocking layer was coated the following aqueous composition, to form an adhesive layer of 7 μm thick on the light-blocking layer.

| Composition of Coating Solution for Adhesive Layer | |
|---|---|
| Alkali-treated gelatin | 4 g(9.3 g/m$^2$) |
| Nonylphenoxy polyethoxyethanol (average oxyethylene unit content: 15) | 0.1 g(0.23 g/m$^2$) |
| Water | 60 g |

The aqueous composition was coated in such an amount that the alkali-treated gelatin in the composition was present in an amount of 9.3 g/m$^2$ (per surface area of the support).

Independently, a knitted fabric (average thickness: 250 μm) composed of polyethylene terephthalate spinning yarn (50 deniers) was subjected to glow discharge treatment to make it hydrophilic.

Subsequently, to the surface of the adhesive layer having been wetted with water in an amount of 30 g/m$^2$ to cause swelling of the layer, was attached the knitted fabric having been treated as above by a pressure laminating method, to form a spreading layer on the adhesive layer.

On the surface of the spreading layer was coated the following pyruvate-containing ethanolic composition in an amount of 100 ml/m².

| Composition of Ethanolic Dispersion of Pyruvate | |
|---|---|
| Ethanol | 500 ml |
| Nonylphenoxy polyethoxyethanol (average oxyethylene unit content: 40) | 5 g(1.0 g/m²) |
| 2-Amino-2-methyl-1,3-propanediol | 9 g(1.8 g/m²) |
| Lipoprotein lipase | 11,400 U(2,280 u/m²) |
| Sodium pyruvate | 1 g(0.2 g/m²) |
| Water | 2 g |

The above composition was prepared by initially preparing an ethanolic composition comprising the components except sodium pyruvate and water and then dropwise adding an aqueous sodium pyruvate solution to the ethanolic composition under stirring.

The resulting multilayer sheet was then dried to prepare an integral multilayer analytical element for quantitative determination of neutral fat.

The analytical element was cut into square tips (1.5 mm×1.5 mm), and each of the tips was placed on a plastic mount disclosed in Japanese Patent Provisional Publication No. 57(1982)-63452, to produce a chemical analytical slide for quantitative determination of neutral fat.

Each of the slides was spotted with 10 µl of various human sera having different concentrations of neutral fat (62, 167, 238, 33, 527, and 659 mg/dl, determined by glycerol-3-phosphate method) and incubated at 37° C. for 6 minutes. Then, each of the slides was measured on the reflective optical density from the PET support side at a light of 540 nm (central wavelength) to prepare a calibration curve. The obtained calibration curve is numerically set out in Table 1.

The analytical element was kept at 45° C. for one week and an aqueous 7% albumin solution was spotted on the element to photometrically measure fog produced in the element. The results are set forth in Table 2.

Aqueous LDH solutions having different LDH activities were prepared by adding a pig heart-originating lactate dehydrogenase (LDH) to a human serum. The above-described measurement procedure was repeated to form another calibration curve for the LDH-coexisting human serum samples. The obtained calibration curve is numerically set out in Table 3.

Comparison Example 1

An analytical element was prepared in the same manner as in Example 1 except that sodium pyruvate of the same amount was incorporated into the underlying reagent layer. Then, two calibration curves were prepared in the same manner as in Example 1, using the prepared analytical element. Also, the measurement of fog after storage of the analytical element was carried out. The results are set forth in the following Tables.

Comparison Example 2

An analytical element was prepared in the same manner as in Example 1 except that no sodium pyruvate was incorporated. Then, two calibration curves were prepared in the same manner as in Example 1, using the prepared analytical element. Also, the measurement of fog after storage of the analytical element was carried out. The results are set forth in the following Tables.

TABLE 1

| Concentration of Neutral Fat (mg/dl) | Example 1 (OD.) | Com. Ex. 1 (OD.) | Com. Ex. 2 (OD.) |
|---|---|---|---|
| 62 | 0.284 | 0.284 | 0.287 |
| 167 | 0.479 | 0.472 | 0.480 |
| 238 | 0.600 | 0.593 | 0.583 |
| 383 | 0.793 | 0.770 | 0.785 |
| 527 | 1.041 | 1.030 | 1.028 |
| 659 | 1.166 | 1.158 | 1.163 |

TABLE 2

| (Occurrence of Fog) | | | |
|---|---|---|---|
| | Example 1 (OD.) | Com. Ex. 1 (OD.) | Com. Ex. 2 (OD.) |
| Immediately after the preparation | 0.162 | 0.165 | 0.163 |
| After one week at at 45° C. | 0.168 | 0.245 | 0.171 |

TABLE 3

| LDH Concentration in Test Solution (mg/dl) | Measured Neutral Fat Concentration (mg/dl) | | |
|---|---|---|---|
| | Example 1 | Com. Ex. 1 | Com. Ex. 2 |
| 160 | 160 | 160 | 163 |
| 340 | 162 | 160 | 165 |
| 740 | 162 | 162 | 178 |
| 1150 | 162 | 165 | 172 |
| 1590 | 163 | 167 | 176 |
| 1970 | 164 | 167 | 180 |
| 2380 | 165 | 168 | 191 |

The results set forth in Tables 1, 2 and 3 clearly indicate that the analytical element of Example 1 according to the present invention is superior to other analytical elements of Comparison Examples 1 and 2.

I claim:

1. A dry multilayer analytical element comprising a light-transmissive, water-impermeable support and at least two reagent layers provided on the support, the reagent layers containing dehydrogenase, pyruvate, NAD+ or NADP+ coenzyme, an electron transport compound and an electron acceptor dye-forming compound wherein the coenzyme is contained in a layer other than a layer containing pyruvate and the electron acceptor dye-forming compound is contained in a layer other than the layer containing pyruvate.

2. The analytical element as claimed in claim 1, wherein the layer containing pyruvate is arranged on the layer or layers containing the coenzyme and the dye-forming compound.

3. The analytical element as claimed in claim 1, wherein the pyruvate is dispersed in a hydrophilic polymer.

4. The analytical element as claimed in claim 1, wherein the pyruvate is selected from the group consisting of sodium pyruvate, potassium pyruvate and lithium pyruvate.

5. The analytical element as claimed in claim 1, wherein the dye-forming compound is a tetrazolium salt.

6. The analytical element as claimed in claim 1, wherein the reagent layers contain a buffer agent to adjust their pH value within pH 7.8 and pH 10.5 after receiving a liquid sample therein.

7. The analytical element as claimed in claim 1 wherein the electron acceptor dye-forming compound is contained in the layer containing coenzyme.

8. The analytical element as claimed in claim 1 wherein the layer containing the electron acceptor dye-forming compound is other than the layer containing coenzyme.

9. A process for the preparation of a dry multilayer analytical element having at least two layers containing a dehydrogenase, $NAD^+$ or $NADP^+$ coenzyme, a pyruvate, an electron transport compound and an electron acceptor dye-forming compound provided on a light-transmissive, water-impermeable support which comprises the steps of:

coating on said support a reagent layer containing at least said coenzyme and electron acceptor dye-forming compound dispersed in a hydrophilic polymer;

coating a spreading layer having a metering effect;

coating a solution or dispersion containing at least said pyruvate in an organic solvent which does not cause substantial swelling of the hydrophilic polymer in the underlying reagent layer, over the spreading layer; and drying the coated layers.

10. A process for the preparation of a dry multilayer analytical element having at least two reagent layers containing a dehydrogenase, $NAD^+$ or $NADP^+$ coenzyme, a pyruvate, an electron transport compound and an electron acceptor dye-forming compound provided on a light-transmissive, water-impermeable support which comprises the steps of:

coating on said support a reagent layer containing at least said coenzyme and electron acceptor dye-forming compound dispersed in a hydrophilic polymer;

coating a solution or dispersion containing at least said pyruvate in an organic solvent which does not cause substantial swelling of the hydrophilic polymer in the underlying reagent layer over the underlying reagent layer; and drying the coated layers.

* * * * *